United States Patent
Tajima et al.

(10) Patent No.: US 7,182,939 B2
(45) Date of Patent: Feb. 27, 2007

(54) HAIR TONIC COMPOSITION

(75) Inventors: Masahiro Tajima, Yokohama (JP);
Youichi Shimatani, Tokyo (JP);
Masashi Ogou, Tokyo (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 10/113,940

(22) Filed: Apr. 2, 2002

(65) Prior Publication Data

US 2002/0192177 A1 Dec. 19, 2002

Related U.S. Application Data

(63) Continuation of application No. 09/421,950, filed on Oct. 21, 1999, now abandoned.

(30) Foreign Application Priority Data

Oct. 26, 1998 (JP) ............................. 10-321287

(51) Int. Cl.
*A61K 7/06* (2006.01)
(52) U.S. Cl. .................. 424/69; 536/27.6; 514/23
(58) Field of Classification Search ........... 536/27.1, 536/27.3, 27.13, 27.2, 27.21, 27, 27.6; 514/42, 514/43, 45, 46, 47, 23; 424/400, 401, 70.1, 424/69
See application file for complete search history.

(56) References Cited

U.S. PATENT DOCUMENTS

| | | | |
|---|---|---|---|
| 4,088,756 A | 5/1978 | Voorhees | |
| 4,839,164 A | 6/1989 | Smith | |
| H001480 H | * 9/1995 | Luo | ........................... 424/400 |

FOREIGN PATENT DOCUMENTS

| | | | |
|---|---|---|---|
| DE | 195 45 107 | | 6/1997 |
| GB | 1 408 036 | | 10/1975 |
| JP | 63088112 | * | 4/1988 |
| JP | 63088112 A | * | 4/1988 |
| JP | 64-042416 | * | 2/1989 |
| JP | 01042416 A | * | 2/1989 |
| JP | 02-311411 | * | 12/1990 |
| JP | 02311411 A | * | 12/1990 |

OTHER PUBLICATIONS

Kunapuli et al., "P2 Receptor subtypes in the cardiovascular system", Biochem. J. (1998) 336, 513-523.*
Klinger et al., "Adenosine Receptors . . . " Cellurlar Signalling 14 (2002) 99-108.*
Hideoki Ogawa; "*Regulation Mechanisms of Hair Growth*"; Normal and Abnormal Epidermal Differentiation; Proceedings of the Japan-U.S. Seminar on Normal and Abnormal Epidermal Differentiation held in 1982; pp. 159-171; University of Tokyo Press, Japan (1983).
Patent Abstracts of Japan, vol. 15, No. 100, Mar. 1991, & JP 02 311411 (Kobayashi Kose Co., Ltd), Dec. 27, 1990, Abstract.
Patent Abstracts of Japan, vol. 18, No. 282, May 1994, & JP 06 048925 (Lion Corp.), Feb. 22, 1994, Abstract.

* cited by examiner

*Primary Examiner*—James O. Wilson
*Assistant Examiner*—Paul V. Ward
(74) *Attorney, Agent, or Firm*—Foley & Lardner LLP

(57) ABSTRACT

A hair tonic composition containing adenosine, adenosine 5'-phosphate, and/or an adenosine 5'-phosphate salt as an active ingredient.

6 Claims, 1 Drawing Sheet

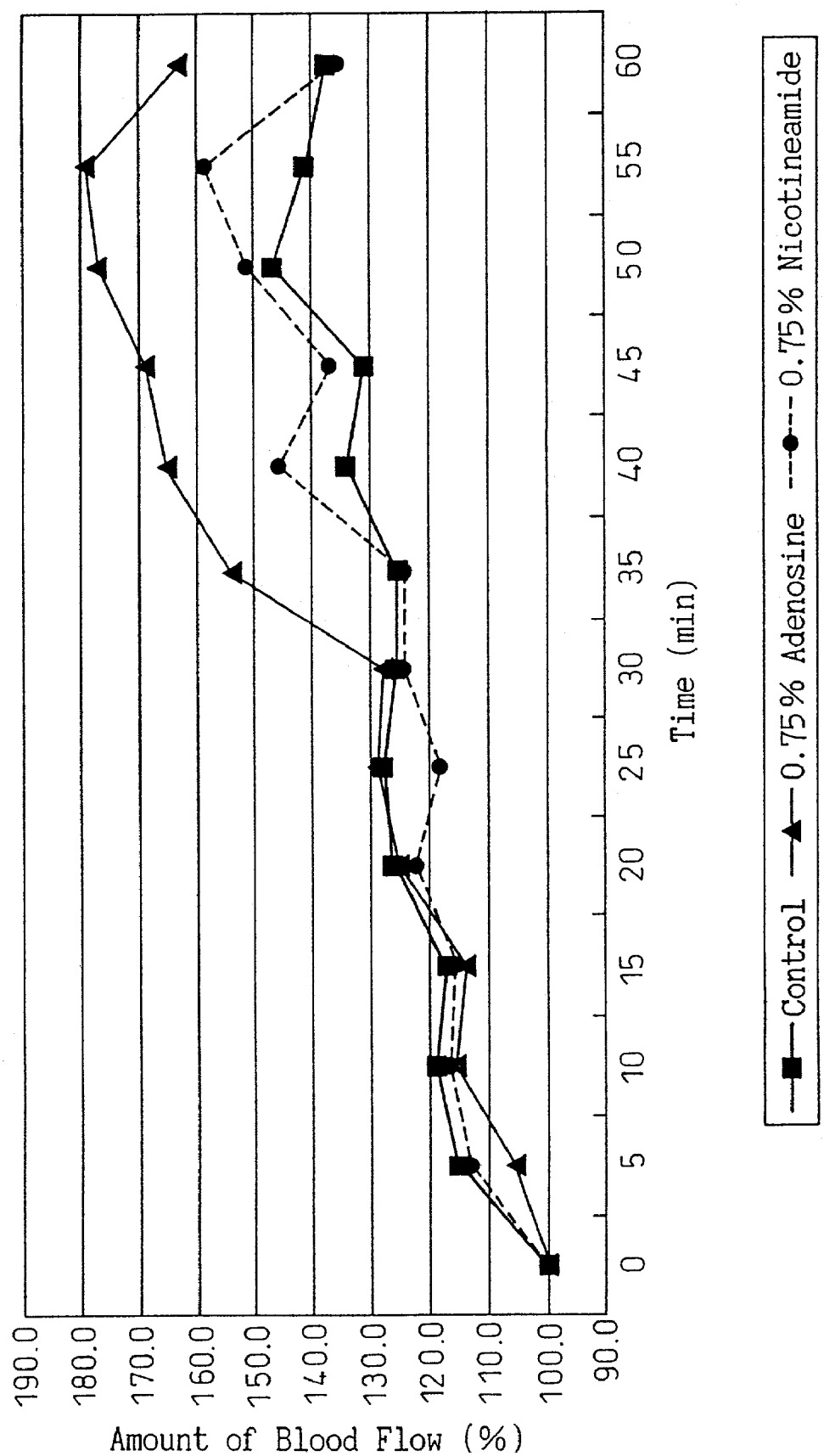

HAIR TONIC COMPOSITION

This application is a continuation-in-part of U.S. application Ser. No. 09/421,950 filed on Oct. 21, 1999, now abandoned.

BACKGROUND OF THE INVENTION

1. Field of the Invention

The present invention is an invention belonging to the field of hair tonics. More particularly, it relates to a hair tonic composition having hair care actions such as a superior hair loss preventing action, hair growth promoting action. The hair tonic composition of the present invention is specifically utilized in the pharmaceutical, quasi-pharmaceutical, or cosmetic fields.

2. Description of the Related Art

In contemporary society, where the percentage of senior citizens in the population is growing and stress is high, there are increasing chances of people being exposed to the danger of hair loss.

In general, hair loss is believed to be caused by the activation of male hormones in the hair follicles, sebaceous glands, and other parts of the body, the decrease in the flow of blood to the hair papilla and hair follicles, hypersteatosis, abnormalities on the scalp due to production of peroxides etc., poor nutrition, etc.

Therefore, conventional hair tonic compositions have generally been formulated with ingredients having actions in eliminating or alleviating these causes.

For example, in order to improve the circulation of blood at the scalp, vasodilators such as swertia herb extract, vitamin E and its derivatives, acetylcholine derivatives, and skin function promoters such as cepharanthine are formulated. To suppress inflammation of the scalp arising due to hypersteatosis etc., antipyrotics such as shikon extract are formulated. To suppress male hormones, female hormones such as estradiol are formulated. Further, to enrich the hair follicles etc., amino acids such as serine and methione, vitamins such as vitamin $B_6$, etc. are formulated. These are used for the purpose of the prevention of hair loss, the promotion of hair growth, etc.

While various attempts have been made as explained above, conventional hair tonics have not necessarily had sufficient hair care actions such as prevention of hair loss and promotion of hair growth. This is probably due to the fact that there are various causes for hair loss or the mechanism of hair growth is extremely complicated. Considering the diversity of reasons for hair loss and the complexity of the mechanism of hair growth, it is desirable to provide a novel hair tonic composition having superior hair care actions.

SUMMARY OF THE INVENTION

Accordingly, the objects of the present invention are to obviate the problems in the prior art and to provide a novel hair tonic composition having superior hair care actions.

In accordance with the present invention, there is provided a hair tonic composition comprising,
 at least one active ingredient selected from the group consisting of adenosine, adenosine 5'-phosphates, and salts of adenosine 5'-phosphates; and
 a carrier therefor.

BRIEF DESCRIPTION OF THE DRAWINGS

The present invention will be better understood from the description set forth below with reference to the accompanying drawing of FIG. 1, which is a graph showing the results of blood flow acceleration effect of the adenosine.

DESCRIPTION OF THE PREFERRED EMBODIMENTS

The present inventors engaged in broad studies on various substances to solve the problem and, as a result, found that adenosine, adenosine 5'-phosphates and/or the salts of adenosine 5'-phosphates have superior hair care actions such as hair loss preventing action and hair growth promoting action, whereby the present invention has been completed.

That is, the present invention provides a hair tonic composition containing adenosine, adenosine 5'-phosphates and/or -the salts of adenosine 5'-phosphates as an active ingredient.

Note that in the present invention, the "hair care" is used in the sense including a hair loss preventing action and a hair growth promoting action. Further, the hair tonic composition of the present invention may be used as an external skin application composition such as a medicinal cosmetic composition for hair care.

The present invention will now be explained in detail.

The hair tonic composition of the present invention, as explained above, contains, as an active ingredient, adenosine, adenosine 5'-phosphates, and/or the salts of adenosine 5'-phosphates.

The adenosines capable of formulating, as an active ingredient, in the hair tonic composition of the present invention is one type of ribonucleoside and contains a purine derivative, adenine, at the base portion thereof. Adenosine 5'-phosphate is also called 5'-adenylic acid and is a nucleotide having one phosphate molecule bonded to the 5'-position hydroxyl group of the ribose of adenosine.

Further, in the salt of adenosine 5'-phosphate, as the counter ion for forming the salt, any substance may be used so long as forming an acid and counter ions. For example, sodium, potassium, calcium, etc. may be mentioned. Further, it is also possible to use the hydrate as the salt of adenosine 5'-phosphate.

In the hair tonic composition of the present invention, it is possible to use, as the adenosine, adenosine 5'-phosphates, and the salts of adenosine 5'-phosphate, those which are commercially available as reagents.

The content of the adenosine, adenosine 5'-phosphates, and/or the salts of adenosine 5'-phosphates in the hair tonic composition of the present invention can be varied depending upon the form, method of application, etc. of the hair tonic composition of the present invention, but in general is 0.01 to 20.0% by weight, preferably 0.1 to 10.0% by weight. If the content is less than 0.01% by weight of the total weight of the hair tonic composition, the desired effect of the present invention does not tend to be sufficiently obtained, and therefore, this is not preferable, while if the amount is more than 20.0% by weight, there is a remarkable tendency of causing problems in the preparation, and therefore is again not preferred.

The type of preparation which the hair tonic composition of the present invention may take is not particularly limited so long as it is a type of preparation which can be applied to the skin, in particular, the scalp. For example, a liquid, emulsion, ointment, etc. may be selected. Further, the hair tonic composition of the present invention may be of any form such as a tonic, hair cream, mousse, shampoo, rinse, etc.

The hair tonic composition of the present invention may further contain, in addition to the above essential ingredients, if necessary, and to an extent not detracting from the desired effect of the present invention, various ingredients generally used in cosmetics, quasi-pharmaceuticals, pharmaceuticals, etc. such as oils, humectants, thickeners, antibacterial agents, medicines, antioxidants, UV blockers, fragrances, coloring agents, surfactants, water, and ethanol.

As the oil, for example, solid paraffin, liquid paraffin, silicone oil, squalane, glyceryl monooleate, olive oil, a higher alcohol, a higher aliphatic acid, isopropyl myristate, etc. may be mentioned.

As the humectants, for example, a polyhydric alcohol, for example, glycerol, propylene glycol, hyaluronic acid, maltitol, atelocollagen, sodium lactate, etc. may be mentioned.

As the thickener, for example, a quince mucilage, carboxyvinyl polymer, xanthane gum, etc. may be mentioned.

As the antibacterial agent, hinokitiol, hexachlorophene, benzalkonium chloride, cetylpyridinium chloride, undecylenic acid, trichlorocarbanilide, bithionol, etc. may be mentioned.

As the medicine, vasodilators such as nicotinamide, benzyl nicotinate, vitamin E or its derivatives, for example, vitamin E acetate, swertia herb extract, calpronium chloride, and acetylcholine; skin function promoters such as cepharanthine; glycyrrhetinic acid or its derivatives; antipyrotics such as shikon extract; female hormones such as estradiol and estrogen; amino acids such as serine, methionine, and arginine; vitamins such as vitamin A, vitamin $B_1$, vitamin $B_6$, biotin, pantothenic acid or its derivatives; and nucleic acids such as adenine, cytosine, thymine, and guanine may be mentioned.

Further, if necessary, medicines such as salicylic acid, zinc or its derivatives, and lactic acid or its alkyl esters; refrigerants such as menthol; and organic acids such as citric acid may be mixed in to an extent not detracting from the desired effect of the present invention.

The hair tonic composition of the present invention may be administered transdermally through direct coating or spraying on the skin. Further, the dosage of the hair tonic composition of the present invention differs depending on age, personal differences, states of the disease, form of the hair tonic composition, etc. and cannot be clearly specified, but when administered to humans, the dosage is one by which adenosine, adenosine 5'-phosphates, and/or the salts of adenosine 5'-phosphates are given in an amount of generally 0.01 to 100.0 mg, preferably 0.1 to 10.0 mg, per kilogram body weight per day. This amount is preferably administered once a day or divided into two to four applications a day.

The hair tonic composition of the present invention has both a superior hair loss preventing action and hair growth promoting action and hair care action in humans and other mammals and is useful as a pharmaceutical, quasi-pharmaceutical, or cosmetic composition for hair care.

EXAMPLES

The present invention will now be explained in further detail with reference to, but is not limited to, the following Examples. In the following Examples, etc., the "%" means % by weight, unless otherwise indicated.

First, formulations of the hair tonic composition of the present invention will be given as Examples.

Example 1

Preparation of Liquid Hair Tonic Composition

| Ingredient | Content (wt %) |
|---|---|
| Adenosine | 3.0 |
| 70% Ethanol | 90.0 |
| Hydrogenated castor oil ethylene oxide (40 mol) adduct | 1.0 |
| Ion exchanged water | Balance |

Method of Production

Adenosine was mixed and stirred with 70% ethanol, hydrogenated castor oil ethylene oxide (40 mol) adduct and a part of the ion exchanged water to obtain a solution. The remainder of the ion exchanged water was added to the solution obtained which was again stirred whereby a liquid hair tonic composition 1 was obtained.

Example 2

Preparation of Liquid Hair Tonic Composition

| Ingredient | Content (wt %) |
|---|---|
| Adenosine 5'-phosphate | 0.5 |
| 70% Ethanol | 90.0 |
| Sodium oleate | 0.01 |
| Dodecylbenzenesulfonic acid | 0.4 |
| Hydrogenated castor oil ethylene oxide (40 mol) adduct | 0.5 |
| Ion exchanged water | Balance |

Method of Production

Adenosine 5'-phosphate was mixed and stirred with 70% ethanol, sodium oleate, dodecylbenzenesulfonic acid, hydrogenated castor oil ethylene oxide (40 mol) adduct, and a part of the ion exchanged water to obtain a solution. The remainder of the ion exchanged water was added to the solution obtained which was again stirred whereby a liquid hair tonic composition 2 was obtained.

Examples 3 and 4

Preparation of Liquid Hair Tonic Composition

| Ingredient | Content (wt %) |
|---|---|
| 2-Sodium adenosine 5'-phosphate or 2-Potassium adenosine 5'-phosphate | 1.0 |
| 70% Ethanol | 90.0 |
| Sorbitan sesquioleate | 0.4 |
| Hydrogenated castor oil ethylene oxide (40 mol) adduct | 0.6 |
| Ion exchanged water | Balance |

Method of Production 2-sodium adenosine 5'-phosphate or 2-potassium adenosine 5'-phosphate was mixed and stirred with 70% ethanol, sorbitan sesquioleate, hydrogenated castor oil ethylene oxide (40 mol) adduct, and part of the ion exchanged water to make it dissolve. The remainder of the ion exchanged water was added to the obtained solution which was again stirred to mix it and thereby obtain liquid hair tonics 3 and 4.

Example 5

Preparation of Liquid Hair Tonic Composition

| Ingredient | Content (wt %) |
|---|---|
| Sodium adenosine 5'-phosphate dihydrate | 0.3 |
| 70% Ethanol | 90.0 |
| Lauroyl taurine | 0.1 |
| Cetylpyridinium chloride | 0.01 |
| Hydrogenated castor oil ethylene oxide (40 mol) adduct | 0.89 |
| Ion exchanged water | Balance |

Method of Production

Sodium adenosine 5'-phosphate dihydrate was mixed and stirred with the 70% ethanol, lauroyl taurine, cetylpyridinium chloride, hydrogenated castor oil ethylene oxide (40 mol) adduct, and a part of the ion exchanged water to obtain a solution. The remainder of the ion exchanged water was added to the solution obtained which was again stirred, whereby a liquid hair tonic composition 5 was obtained.

Next, the hair growth promoting actions of the hair tonic compositions 1 to 5 obtained in the Examples 1 to 5 were evaluated. Further, the hair care actions of the hair tonic compositions 1 and 3 were evaluated.

Hair Growth Promoting Action Test As experimental animals, C3H/HeNCrJ mice in the resting stage of the hair cycle were used. The test was conducted by the method of Ogawa et al. (*Normal and Abnormal Epidermal Differentiation*, M. Seiji and I. A. Bernstein ed., pp. 159 to 170, 1982, Tokyo University Press).

That is, six groups of 10 mice each were prepared. The hair was shaved off from the back of the mice by shears and shavers, then the test samples (hair tonic compositions 1 to 5) or a control sample (70% ethanol solution) were coated on the shaved portions of the mice in the groups once a day in amounts of 0.1 ml a time. The area of regrowth of hair was measured after 25 days.

The results are shown in Table 1 where numerical values are mean values.

TABLE 1

| Sample | Area of hair regrowth (%) | Sample | Area of hair regrowth (%) |
|---|---|---|---|
| Hair tonic 1 | 96 | Hair tonic 2 | 65 |
| Hair tonic 3 | 75 | Hair tonic 4 | 55 |
| Hair tonic 5 | 45 | Control | 2.0 |

As clear from Table 1, the hair tonic composition of the present invention exhibits a significant effect in the hair growth promoting action test on mice. It was found that the hair tonic composition of the present, invention has a superior hair growth promoting action.

Hair Care Action Test

The hair care action, including the hair loss preventing action and the hair growth promoting action, of the hair tonic composition of the present invention was investigated by application of a trichogram test on human subjects by the following method. The test samples were the hair tonic compositions 1 and 3 used for the above hair growth test, while the control sample was 70% ethanol.

That is, the hair tonic compositions 1 and 3 and 70% ethanol as the control were each coated on the scalps of 100 male test subjects twice a day in 2 ml amounts each time for six months straight. One hundred hairs were pulled from each test subject directly before coating and directly after ending the coating after six months. The hair roots of the pulled out hairs were observed under a microscope to count the number of hair roots in the resting stage from the state of the hair roots and find the ratio of the resting stage hair roots.

The hair care actions of the test samples (i.e., hair tonic compositions 1 and 3) and the control sample (70% ethanol) were compared by the change in the ratio of resting stage hair roots. Resting stage hair roots are hair roots of hair which have stopped growing. Persons complaining of hair loss are observed to have a greater ratio of such resting stage hair roots than normal persons.

The hair care action was evaluated based on the following criteria:

Criteria

Effective: At least 40% of test subjects experience at least 20% reduction in ratio of resting stage hair roots Somewhat effective: At least 20% of test subjects experience at least 20% reduction in ratio of resting stage hair roots Ineffective: Less than 20% of test subjects experience at least 20% reduction in ratio of resting stage hair roots The results are shown in Table 2.

TABLE 2

| | Ratio of test subjects experiencing different changes of resting stage hair roots (%) | | | |
|---|---|---|---|---|
| Sample | Reduced at least 20% | Reduced less than 20% or increased less than 20% | Increased at least 20% | Evaluation of hair care action |
| Hair tonic 1 | 42 | 33 | 25 | Effective |
| Hair tonic 3 | 35 | 30 | 35 | Somewhat effective |
| Control | 10 | 50 | 40 | Ineffective |

From the results of Table 2, it became clear that hair tonic composition of the present invention containing adenosine or salts of adenosine 5'-phosphate exhibits significant hair care action in human trichogram tests.

Further, since a hair growth promoting action was observed even in the hair tonic composition of the present invention containing adenosine 5'-phosphate (hair tonic 2), it was clear that a similar hair care action is observed even in the hair tonic of the present invention containing adenosine 5'-phosphate.

In addition to Examples 1 to 5, formulations of hair tonic compositions of other embodiments of the present invention are shown as Examples. All of the hair tonic compositions obtained in the following Examples were observed to have hair growth promoting actions and hair care actions substantially the same as the above liquid hair tonic compositions 1 to 5.

Example 6

Preparation of Liquid Hair Tonic Composition

| Ingredient | Content (wt %) |
| --- | --- |
| (Phase A) | |
| 2-Sodium adenosine 5'-phosphate | 1.0 |
| Hydrogenated castor oil ethylene oxide (60 mol) adduct | 2.0 |
| Glycerol | 10.0 |
| Dipropylene glycol | 10.0 |
| 1,3-Butylene glycol | 5.0 |
| Polyethylene glycol 1500 | 5.0 |
| (Phase B) | |
| Cetyl isooctanate | 10.0 |
| Squalane | 5.0 |
| Vaseline | 2.0 |
| Propyl paraben | 2.0 |
| (Phase C) | |
| 1% Aqueous solution of carboxyvinyl polymer | 30.0 |
| Sodium hexametaphosphate | 0.03 |
| Ion exchanged water | 8.35 |
| (Phase D) | |
| Ion exchanged water | 4.5 |
| (Phase E) | |
| Potassium hydroxide | 0.12 |
| Ion exchanged water | 5.0 |

Method of Production

Phase A and Phase B were heated at 60° C. to dissolve the ingredients, then mixed and processed by a homomixer to obtain a gel. Phase D was gradually added thereto and, dispersed therein by the homomixer.

Next, the solution of Phase C was added thereto, then finally the solution of Phase E was added and the resultant emulsified by a homomixer to obtain an O/W emulsion type hair tonic composition.

Example 7

Preparation of Cream Hair Tonic Composition

| Ingredient | Content (wt %) |
| --- | --- |
| (Phase A) | |
| Liquid paraffin | 5.0 |
| Cetostearyl alcohol | 5.5 |
| Glyceryl monostearate | 3.0 |
| EO (20 mol)-2-octyldodecyl ether | 3.0 |
| Propyl paraben | 0.3 |
| Fragrance | 0.1 |
| (Phase B) | |
| Adenosine | 5.0 |
| Glycerol | 8.0 |
| Dipropylene glycol | 20.0 |
| Polyethylene glycol 4000 | 5.0 |
| Sodium dodecyl sulfate | 0.1 |
| Sodium hexametaphosphate | 0.005 |
| Ion exchanged water | Balance |

Method of Production

Phase A and Phase B were heated to dissolve the ingredients, then emulsified by a homomixer to obtain a cream state hair tonic composition.

Example 8

Preparation of Liquid Hair Tonic Composition

| Ingredient | Content (wt %) |
| --- | --- |
| Potassium adenosine 5'-phosphate | 0.5 |
| Stearyl dimethyl amine oxide | 0.5 |
| Hydrogenated castor oil ethylene oxide (40 mol) adduct | 1.0 |
| 95% Ethanol | 54.0 |
| Ion exchanged water | Balance |

Method of Production

The ion exchanged water was added to 95% ethanol, then the hydrogenated castor oil ethylene oxide (40 mol) adduct and stearyl dimethyl amine oxide were added, then the potassium adenosine 5'-phosphate was added and the mixture stirred to dissolve and obtain the liquid hair tonic composition.

Example 9

Preparation of Liquid Hair Tonic Composition

| Ingredient | Content (wt %) |
| --- | --- |
| Sodium N-cocolauryl-β-aminopropionate | 0.2 |
| 2-Sodium adenosine 5'-phosphate | 1.0 |
| Sodium dodecylbenzenesulfonate | 0.5 |
| Hydrogenated castor oil ethylene oxide (40 mol) adduct | 1.0 |
| 95% Ethanol | 54.0 |
| Ion exchanged water | Balance |

Method of Production

The ion exchanged water was added to 95% ethanol, then the hydrogenated castor oil ethylene oxide (40 mol) adduct, sodium dodecylbenzenesulfonate, and sodium N-cocolauryl-β-aminopropionate were added, then the 2-sodium adenosine 5'-phosphate was added and the mixture was stirred to dissolve and obtain the liquid hair tonic.

Blood Flow Increase Test

The blood flow increasing effect of adenosine was evaluated, compared with the control and nicotineamide, under the following conditions, the results are shown in FIG. 1.

Determination portion: Human upper arm

Sample: 0.75% Adenosine, 0.75% Nicotineamide, placebo preparation

Test method:
1) Allow to stand for 30 minutes within constant temperature and humidity (25° C.) room.
2) The measurement positions A, B and C from the wrist with the distance of 5 cm or more.
3) The positions were subjected to the previous determinations by an Omega-Flow Flo-N1(i.e., Laser Doppler Meter) with three-sets of a probe and a blood flow meter. When the blood flow of the base was remarkably different.

4) 10 μl of each sample was applied with 8 mmφ to the determination points.

5) Monitoring the results.

As explained above, according to the present invention, there is provided a hair tonic composition having superior hair care actions such as a hair loss preventing action and hair growth promoting action in humans and other mammals.

The invention claimed is:

1. A method of promoting hair growth in a human comprising applying, to scalp or hair roots of said human, a composition containing, as an active ingredient, an effective amount of adenosine and a carrier therefor.

2. The method as claimed in claim 1, wherein the amount of the active ingredient is 0.01% to 20.0% by weight, based upon the total weight of the composition.

3. The method as claimed in claim 1, wherein the carrier is selected from the group consisting of oils, humectants, thickeners, antibacterial agents, medicines, antioxidants, UV blockers, fragrances, coloring agents, surfactants, water, and ethanol.

4. The method as claimed in claim 3, wherein the oil is selected from the group consisting of solid paraffin, liquid paraffin, silicone oil, squalane, glyceryl monooleate, olive oil, a higher alcohol, a higher aliphatic acid and isopropyl myristate.

5. The method as claimed in claim 2, wherein the carrier is selected from the group consisting of oils, humectants, thickeners, antibacterial agents, medicines, antioxidants, UV blockers, fragrances, coloring agents, surfactants, water, and ethanol.

6. The method as claimed in claim 5, wherein the oil is selected from the group consisting of solid paraffin, liquid paraffin, silicone oil, squalane, glyceryl monooleate, olive oil, a higher alcohol, a higher aliphatic acid and isopropyl myristate.

* * * * *